US008668651B2

(12) United States Patent
Burnes et al.

(10) Patent No.: US 8,668,651 B2
(45) Date of Patent: Mar. 11, 2014

(54) ECG LEAD SET AND ECG ADAPTER SYSTEM (75) Inventors: Lee Burnes, Wilbraham, MA (US); Scott Coggins, Palmer, MA (US); Dawn Moore, Belchertown, MA (US); Dave Selvitelli, Suffield, CT (US); Mark Tauer, Belchertown, MA (US); Kathleen Tremblay, Westfield, MA (US)

(73) Assignee: Covidien LP, Mansfield, MA (US)

( * ) Notice: Subject to any disclaimer, the term of this patent is extended or adjusted under 35 U.S.C. 154(b) by 1109 days.

(21) Appl. No.: 11/633,709

(22) Filed: Dec. 5, 2006

(65) Prior Publication Data

US 2008/0132106 A1 Jun. 5, 2008

(51) Int. Cl.
*A61B 5/0402* (2006.01)

(52) U.S. Cl.
USPC ............ 600/508; 600/509; 600/393; 600/372

(58) Field of Classification Search
USPC ............. 600/393, 509, 372, 439, 508; 607/37
See application file for complete search history.

(56) References Cited

U.S. PATENT DOCUMENTS

| 3,606,881 A | 9/1971 | Woodson |
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,895,635 A | 7/1975 | Justus et al. |
| 3,901,218 A | 8/1975 | Buchalter |
| 3,997,225 A | 12/1976 | Horwinski |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,112,941 A | 9/1978 | Larimore |
| 4,166,465 A | 9/1979 | Esty et al. |
| 4,256,118 A | 3/1981 | Nagel |
| 4,353,372 A | 10/1982 | Ayer |

(Continued)

FOREIGN PATENT DOCUMENTS

| DE | 90 02 539 | 3/1990 |
| DE | 90 02 539 U1 | 5/1990 |

(Continued)

OTHER PUBLICATIONS

International Search Report EP07253850 dated Dec. 21, 2007.

(Continued)

*Primary Examiner* — Joseph Stoklosa
(74) *Attorney, Agent, or Firm* — Lisa E. Winsor, Esq.

(57) ABSTRACT

A method for coupling an ECG monitor with an incompatible ECG lead set includes the steps of providing an ECG adapter including an adapter body having at least one monitor connector adapted for coupling to an input of an ECG monitor and at least one lead set receptacle adapted for coupling to a connector of an ECG lead set incompatible with the input of the ECG monitor, coupling the at least one monitor connector of the adapter body with the input of the ECG monitor and coupling the at least one lead set receptacle of the adapter body with the connector of the ECG lead set to thereby electrically couple the ECG lead set with the ECG monitor.

11 Claims, 6 Drawing Sheets

(56) References Cited

U.S. PATENT DOCUMENTS

| | | |
|---|---|---|
| 4,365,634 A | 12/1982 | Bare et al. |
| 4,378,021 A | 3/1983 | Strand |
| 4,385,272 A | 5/1983 | Whitehead |
| 4,477,801 A | 10/1984 | Robinson et al. |
| 4,498,480 A | 2/1985 | Mortensen |
| 4,729,377 A | 3/1988 | Granek et al. |
| 4,763,660 A | 8/1988 | Kroll et al. |
| 4,781,200 A | 11/1988 | Baker |
| 4,785,822 A | 11/1988 | Wallace |
| 4,815,964 A | 3/1989 | Cohen et al. |
| 4,850,356 A | 7/1989 | Heath |
| 4,909,260 A | 3/1990 | Salem et al. |
| 4,947,846 A | 8/1990 | Kitagawa et al. |
| 4,957,109 A | 9/1990 | Groeger et al. |
| 5,080,604 A | 1/1992 | Rider et al. |
| 5,083,238 A | 1/1992 | Bousman |
| 5,083,933 A | 1/1992 | Colleran et al. |
| 5,104,253 A | 4/1992 | Zielinski et al. |
| 5,104,334 A | 4/1992 | Honma et al. |
| 5,131,854 A | 7/1992 | Jose et al. |
| 5,137,466 A | 8/1992 | Endo et al. |
| 5,154,646 A | 10/1992 | Shoup |
| 5,158,469 A | 10/1992 | Martin |
| 5,160,276 A | 11/1992 | Marsh et al. |
| 5,173,059 A | 12/1992 | Sato et al. |
| 5,176,343 A | 1/1993 | Cheney, II et al. |
| 5,178,556 A | 1/1993 | Chen |
| 5,180,312 A | 1/1993 | Martin |
| 5,190,467 A | 3/1993 | Ohta |
| 5,192,226 A | 3/1993 | Wang |
| 5,197,901 A | 3/1993 | Hashiguchi |
| 5,199,897 A | 4/1993 | Hashiguchi |
| 5,201,669 A | 4/1993 | Lin |
| 5,203,715 A | 4/1993 | Yamamoto |
| 5,203,719 A | 4/1993 | Kozono |
| 5,207,594 A | 5/1993 | Olson |
| 5,224,479 A | 7/1993 | Sekine |
| 5,232,383 A | 8/1993 | Barnick |
| 5,234,357 A | 8/1993 | Yamaguichi |
| 5,243,510 A | 9/1993 | Cheney, II |
| 5,263,481 A | 11/1993 | Axelgaard |
| 5,276,443 A | 1/1994 | Gates et al. |
| 5,278,759 A | 1/1994 | Berra et al. |
| 5,293,013 A | 3/1994 | Takahashi |
| 5,301,680 A | 4/1994 | Rosenberg |
| 5,320,621 A | 6/1994 | Gordon et al. |
| 5,326,272 A | 7/1994 | Harhen et al. |
| 5,332,330 A | 7/1994 | Kaneko |
| 5,338,219 A | 8/1994 | Hiramoto |
| 5,341,806 A | 8/1994 | Gadsby et al. |
| 5,341,812 A * | 8/1994 | Allaire et al. ................. 600/508 |
| 5,353,793 A | 10/1994 | Bornn |
| 5,362,249 A | 11/1994 | Carter |
| 5,370,116 A | 12/1994 | Rollman et al. |
| 5,370,550 A | 12/1994 | Alwine et al. |
| 5,373,852 A | 12/1994 | Harrison et al. |
| 5,376,016 A | 12/1994 | Inaba et al. |
| 5,378,168 A | 1/1995 | Sumida |
| 5,380,223 A | 1/1995 | Marsh et al. |
| 5,382,176 A | 1/1995 | Norden |
| 5,383,794 A | 1/1995 | Davis et al. |
| 5,387,116 A | 2/1995 | Wang |
| 5,387,127 A | 2/1995 | Wang |
| 5,399,045 A | 3/1995 | Yoneda et al. |
| 5,405,269 A | 4/1995 | Stupecky |
| 5,415,164 A | 5/1995 | Faupel et al. |
| 5,427,111 A | 6/1995 | Traub et al. |
| 5,429,526 A | 7/1995 | Ann |
| 5,442,940 A | 8/1995 | Secker et al. |
| 5,454,739 A | 10/1995 | Strand |
| 5,462,448 A | 10/1995 | Kida et al. |
| 5,486,117 A | 1/1996 | Chang |
| 5,494,032 A | 2/1996 | Robinson et al. |
| 5,507,290 A | 4/1996 | Kelly et al. |
| 5,507,665 A | 4/1996 | Oda |
| 5,507,668 A | 4/1996 | Lambrinos et al. |
| 5,509,822 A | 4/1996 | Negus et al. |
| 5,511,553 A | 4/1996 | Segalowitz |
| 5,546,950 A | 8/1996 | Schoeckert et al. |
| 5,558,535 A | 9/1996 | Saka et al. |
| 5,564,939 A | 10/1996 | Maitani et al. |
| 5,582,180 A | 12/1996 | Manset et al. |
| 5,584,719 A | 12/1996 | Tsuji et al. |
| 5,599,199 A | 2/1997 | Wright |
| 5,603,632 A | 2/1997 | Johannes et al. |
| 5,611,708 A | 3/1997 | Mizunuma et al. |
| 5,613,870 A | 3/1997 | Traver, Jr. |
| 5,615,674 A | 4/1997 | Maurer |
| 5,622,168 A | 4/1997 | Keusch et al. |
| 5,624,271 A | 4/1997 | Childs et al. |
| 5,626,135 A | 5/1997 | Sanfilippo |
| 5,632,274 A | 5/1997 | Quedens et al. |
| 5,651,689 A | 7/1997 | Plyler et al. |
| 5,653,606 A | 8/1997 | Chrysostomou |
| 5,674,088 A | 10/1997 | Roche et al. |
| 5,676,694 A | 10/1997 | Boser et al. |
| 5,679,022 A | 10/1997 | Cappa |
| 5,679,029 A | 10/1997 | Saunier et al. |
| 5,685,303 A | 11/1997 | Rollman et al. |
| 5,694,940 A | 12/1997 | Unger et al. |
| 5,695,355 A | 12/1997 | Hasenfratz et al. |
| 5,702,265 A | 12/1997 | Yamaguchi |
| 5,704,351 A | 1/1998 | Mortara et al. |
| 5,711,684 A | 1/1998 | Inoue et al. |
| 5,718,596 A | 2/1998 | Inaba et al. |
| 5,724,025 A | 3/1998 | Tavori |
| 5,724,984 A | 3/1998 | Arnold et al. |
| 5,725,525 A | 3/1998 | Kordis |
| 5,741,155 A | 4/1998 | Herman |
| 5,749,746 A | 5/1998 | Tan et al. |
| 5,766,133 A | 6/1998 | Faisandier |
| 5,769,650 A | 6/1998 | Aoyama et al. |
| 5,772,591 A | 6/1998 | Cram |
| 5,775,953 A | 7/1998 | Yamanashi et al. |
| 5,782,647 A | 7/1998 | Okura et al. |
| 5,782,892 A | 7/1998 | Castle et al. |
| 5,785,664 A | 7/1998 | Rosenberg |
| 5,788,527 A | 8/1998 | Sanders et al. |
| 5,797,854 A | 8/1998 | Hedgecock |
| 5,806,152 A | 9/1998 | Saitou et al. |
| 5,813,404 A | 9/1998 | Devlin et al. |
| 5,813,979 A | 9/1998 | Wolfer |
| 5,827,086 A | 10/1998 | Fukuda |
| 5,830,000 A | 11/1998 | Shifflett et al. |
| 5,836,783 A | 11/1998 | Morisawa et al. |
| 5,843,141 A | 12/1998 | Bischoff et al. |
| 5,848,456 A | 12/1998 | Sjoqvist |
| 5,865,740 A | 2/1999 | Kelly et al. |
| 5,865,741 A | 2/1999 | Kelly et al. |
| 5,871,451 A | 2/1999 | Unger et al. |
| 5,873,747 A | 2/1999 | Tsuji |
| 5,876,232 A | 3/1999 | Matsushita et al. |
| 5,886,576 A | 3/1999 | Carlson |
| 5,895,284 A | 4/1999 | Kocher et al. |
| 5,904,579 A | 5/1999 | McLean et al. |
| 5,913,834 A | 6/1999 | Francais |
| 5,916,159 A | 6/1999 | Kelly et al. |
| 5,931,689 A | 8/1999 | Patel |
| 5,931,861 A | 8/1999 | Werner et al. |
| 5,934,926 A | 8/1999 | Gabrisko, Jr. et al. |
| 5,935,061 A | 8/1999 | Acker et al. |
| 5,937,950 A | 8/1999 | Adams et al. |
| 5,938,470 A | 8/1999 | Kashiyama |
| 5,938,597 A | 8/1999 | Stratbucker |
| 5,941,725 A | 8/1999 | Brennan et al. |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |

(56) References Cited

U.S. PATENT DOCUMENTS

| | | |
|---|---|---|
| 6,027,359 A | 2/2000 | Aoki et al. |
| 6,032,063 A | 2/2000 | Hoar et al. |
| 6,032,064 A | 2/2000 | Devlin et al. |
| 6,036,533 A | 3/2000 | Huang |
| 6,038,479 A | 3/2000 | Werner et al. |
| 6,038,481 A | 3/2000 | Werner et al. |
| 6,044,283 A | 3/2000 | Fein et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,177,673 B1 | 1/2001 | Blomberg et al. |
| 6,190,385 B1 | 2/2001 | Tom et al. |
| 6,203,354 B1 | 3/2001 | Kuwahara et al. |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky et al. |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,324,432 B1 | 11/2001 | Rigaux et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda et al. |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,450,958 B1 | 9/2002 | Linkhart et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisandier |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wi |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,705,880 B2 | 3/2004 | Rhude |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| 6,805,579 B2 | 10/2004 | Marchand et al. |
| 6,816,744 B2 | 11/2004 | Garfield et al. |
| 6,832,928 B2 | 12/2004 | Suzuki |
| 6,837,734 B2 | 1/2005 | Ushio et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | KenKnight et al. |

(56) References Cited

U.S. PATENT DOCUMENTS

| | | |
|---|---|---|
| 6,945,796 B2 | 9/2005 | Bassler et al. |
| 6,945,807 B1 | 9/2005 | Wu |
| 6,948,973 B1 | 9/2005 | Hsu et al. |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,081,008 B2 | 7/2006 | Tan |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,144,372 B2 | 12/2006 | Ng et al. |
| 7,150,655 B2 | 12/2006 | Mastrototaro et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | LeGallic et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,258,566 B2 | 8/2007 | Koenig et al. |
| 7,264,510 B2 | 9/2007 | Koenig et al. |
| 7,270,568 B2 | 9/2007 | Osypka |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillonville et al. |
| 7,322,849 B2 | 1/2008 | Sutton |
| 7,322,857 B2 | 1/2008 | Chen |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 * | 4/2008 | Erickson et al. ............... 607/27 |
| 7,361,058 B1 | 4/2008 | Lien et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achter et al. |
| 7,462,074 B1 | 12/2008 | Devlin et al. |
| 7,465,187 B1 | 12/2008 | Wu |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| 7,666,028 B2 | 2/2010 | Meleck |
| 7,826,882 B2 | 11/2010 | McIntire et al. |
| 8,109,883 B2 | 2/2012 | Meyer et al. |
| 8,255,041 B2 | 8/2012 | Istvan et al. |
| 2002/0133069 A1 | 9/2002 | Roberts |
| 2002/0137997 A1 | 9/2002 | Mastrototaro et al. |
| 2002/0138011 A1 | 9/2002 | Rantala |
| 2002/0188216 A1 | 12/2002 | Kayyali et al. |
| 2003/0068914 A1 | 4/2003 | Merry et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0164551 A1 | 7/2005 | Wlos |
| 2005/0177052 A1 | 8/2005 | Istvan et al. |
| 2005/0182466 A1 | 8/2005 | Mahajan |
| 2005/0203349 A1 | 9/2005 | Nanikashvili |
| 2006/0073728 A1 | 4/2006 | Zaiken et al. |
| 2006/0286861 A1 | 12/2006 | Avevor et al. |
| 2007/0038057 A1 | 2/2007 | Nam et al. |
| 2007/0260133 A1 | 11/2007 | Meyer |
| 2008/0132106 A1 | 6/2008 | Burnes et al. |
| 2009/0099423 A1 | 4/2009 | Al-Ali et al. |

FOREIGN PATENT DOCUMENTS

| | | |
|---|---|---|
| DE | 102 25 621 B3 | 1/2004 |
| DE | 10 2004 032 410 A1 | 1/2006 |
| DE | 102004032410 | 1/2006 |
| EP | 0 766 946 | 4/1997 |
| EP | 0 766 946 A2 | 4/1997 |
| EP | 0766946 | 4/1997 |
| EP | 0 766 946 A3 | 5/1997 |
| EP | 0 799 628 A | 10/1997 |
| EP | 0 799 628 A2 | 10/1997 |
| EP | 0799628 A2 | 10/1997 |
| EP | 0 799 628 A3 | 3/1999 |
| EP | 1 050 269 A1 | 11/2000 |
| EP | 1050269 | 11/2000 |
| EP | 1 932 470 A1 | 6/2008 |
| EP | 2 070 474 A2 | 6/2009 |
| JP | 1-42055 | 12/1989 |
| JP | 3-13830 | 3/1991 |
| JP | 7-163528 | 6/1995 |
| JP | 11-318921 | 11/1999 |
| JP | 2001-189629 | 7/2001 |
| JP | 2003-10138 | 1/2003 |
| JP | 2003-010138 A | 1/2003 |
| JP | 2004-282608 | 10/2004 |
| JP | 2004-282608 A | 10/2004 |
| WO | WO 03/047427 A2 | 6/2003 |
| WO | WO 2008/092098 A2 | 7/2008 |

OTHER PUBLICATIONS

Andreas Boos et al.; "A New Lightweight Fetal Telemetry System"; Dec. 1995; Hewlett-Packard Journal; pp. 82-93.
International Search Report EP07 25 1765 dated Mar. 31, 2008.
International Search Report EP07 25 4691 dated Mar. 25, 2008.
International Search Report EP08 16 4409 dated Jan. 27, 2009.
European Search Report, Application No. EP 07 25 4691 dated Mar. 25, 2008.

(56) References Cited

OTHER PUBLICATIONS

European Office Action dated Dec. 20, 2011 for European Patent Appln. No. EP 07 253 850.7.
European Search Report for EP 11 00 6002 dated Nov. 15, 2011.
U.S. Appl. No. 13/443,096, filed Apr. 10, 2012, Selvitelli.
Australian Second Examiner's Report dated Mar. 15, 2013 for Australian Patent Application No. 2007237339, 5 pages.
European Search Report corresponding to European Application No. EP 07 25 3850, date of completion is Dec. 21, 2007; 2 pages.
Office Action in Mexican Patent Application No. MX/a/2007/015295, 2 pages.
Office Action in Mexican Patent Application No. MX/A/2012/009542, 2 pages.
A&D Company, Limited, "Vital Sensor Graphic Model", No. TM-2560G/TM2564G-TM-2564GP/TM-2564GP, Jan. 1, 2004, pp. 1-62.
Office Action for U.S. Appl. No. 13/192,022 dated Jan. 3, 2013, 6 pages.
Response to Office Action filed Jan. 22, 2013, 10 pages.
Office Action for U.S. Appl. No. 13/192,022 dated Mar. 13, 2013, 8 pages.
Extended European Search Report for European Application No. 1100600237-1526 dated Nov. 15, 2011, 8 pages.
Response to European Search Report for European Application No. 1100600237-1526 filed Jul. 31, 2012, 6 pages.
Response to Examiner's Report dated May 23, 2012 for Australian Patent Application No. 2007237339 filed Jan. 29, 2013, 12 pages.
Patent Examination Report No. 2 for Australian Patent Application No. 2007237339 dated Mar. 15, 2013, 5 pages.
Examiner's First Report on Australian Patent Application No. 2007237339 dated May 23, 2012, 4 pages.
Chinese Office Action for Chinese Patent Application No. 200710300791.X dated Dec. 6, 2010, 14 pages, (with English translation).
Notification of the Second Office Action for Chinese Patent Application No. 200710300791.X dated Aug. 24, 2011, 8 pages, (with English translation).
Communication pursuant to Article 94(3) EPC for European Patent Application No. 07 254 691.4-1265 dated Nov. 24, 2010, 4 pages.
European Search Report for Application No. 07 25 4691 date Mar. 25, 2008, 6 pages.
Response to Communication Pursuant to Article 94(3) dated Nov. 24, 2010 for European Patent Application No. 07254691.4 filed on Mar. 30, 2011, 3 pages.
Notice of Reasons for Rejection for Japanese Patent Application No. 2007-314074 dated Oct. 12, 2012, 4 pages, (English translation only).
Mexican Office Action for Mexican Patent Application No. MX/a/2007/015295 dated Mar. 8, 2013, 3 pages, (English translation only).
Office Action for U.S. Appl. No. 11/633,709 dated Jun. 1, 2012, 11 pages.
Response to Office Action dated Jun. 1, 2012 in U.S. Appl. No. 11/633,709, filed Nov. 30, 2012, 12 pages.
Office Action for U.S. Appl. No. 11/633,709 dated Jan. 28, 2013, 7 pages.
Office Action in U.S. Appl. No. 11/633,709 dated Jun. 19, 2009, 9 pages.
Response to Office Action in U.S. Appl. No. 11/633,709 dated Jun. 19, 2009 filed Jul. 22, 2009, 2 pages.
Office Action in U.S. Appl. No. 11/633,709 dated Nov. 12, 2009, 7 pages.
Response to Office Action in U.S. Appl. No. 11/633,709 dated Nov. 12, 2009 filed on Feb. 12, 2010, 11 pages.
Office Action in U.S. Appl. No. 11/633,709 dated Jul. 8, 2010, 8 pages.
Response to Office Action in U.S. Appl. No. 11/633,709 dated Jul. 8, 2010 filed on Nov. 8, 2010, 11 pages.

Communication pursuant to Article 94(3) EPC for European Patent Application No. 07 253 850.7-2319 dated Dec. 20, 2011, 5 pages.
Response to Communication pursuant to Article 94(3) EPC for European Patent Application No. 07 253 850.7-2319 dated Dec. 20, 2011 filed Jun. 29, 2012, 3 pages.
Notice of Reasons for Rejection for Japanese Patent Application No. 2007-254792 dated Feb. 8, 2013, 5 pages, (with English translation).
Translation of Mexican Office Action for Mexican Patent Application No. MX/a/2007/012064, 4 pages.
Office Action in U.S. Appl. No. 11/528,914 dated Jul. 17, 2008, 9 pages.
Response to Office Action in U.S. Appl. No. 11/528,914 dated Jul. 17, 2008 filed on Aug. 18, 2008, 3 pages.
Office Action in U.S. Appl. No. 11/528,914 dated Sep. 23, 2008, 9 pages.
Response to Office Action in U.S. Appl. No. 11/528,914 dated Sep. 23, 2008 filed on Jan. 23, 2009, 16 pages.
Office Action in U.S. Appl. No. 11/528,914 dated Apr. 8, 2009, 8 pages.
Response to Office Action in U.S. Appl. No. 11/528,914 dated Apr. 8, 2009 filed on Jun. 8, 2009, 14 pages.
Advisory Action in U.S. Appl. No. 11/528,914 dated Jun. 24, 2009, 3 pages.
Office Action in U.S. Appl. No. 11/528,914 dated Sep. 8, 2009, 11 pages.
Response to Office Action in U.S. Appl. No. 11/528,914 dated Sep. 8, 2009 filed on Dec. 8, 2009, 14 pages.
Office Action in U.S. Appl. No. 11/528,914 dated Feb. 5, 2010, 12 pages.
Response to Office Action in U.S. Appl. No. 11/528,914 dated Feb. 5, 2010 filed on May 5, 2010, 14 pages.
Advisory Action in U.S. Appl. No. 11/528,914 dated May 13, 2010, 3 pages.
Office Action in U.S. Appl. No. 11/528,914 dated Jul. 15, 2010, 9 pages.
Response to Office Action in U.S. Appl. No. 11/528,914 dated Jul. 15, 2010 filed on Oct. 14, 2010, 17 pages.
Office Action in U.S. Appl. No. 11/528,914 dated Dec. 22, 2010, 11 pages.
Response to Office Action in U.S. Appl. No. 11/528,914 dated Dec. 22, 2010 filed on Feb. 18, 2011, 14 pages.
Advisory Action in U.S. Appl. No. 11/528,914 dated Mar. 4, 2011, 3 pages.
Preliminary Amendment in U.S. Appl. No. 11/528,914, filed May 11, 2011, 11 pages.
Notice of Allowability in U.S. Appl. No. 11/528,914 dated Nov. 22, 2011, 4 pages.
Responses to Chinese Office Action in Chinese Application No. 201010624971.5 filed on Apr. 5, 2011, 21 pages.
Notification of Entry into Examination Procedure for Chinese Patent Application No. 201010624971.5 dated Oct. 11, 2012, 2 pages, (with English translation).
Extended European Search Report for European Patent Application No. 10013624.1-2319/2314215 dated Apr. 4, 2011, 14 pages.
Response to Communication dated May 10, 2011 in European Patent Application No. 10013624.1-2319/2314215 filed on Nov. 2, 2011, 5 pages.
Office Action for U.S. Appl. No. 12/876,316 dated Jul. 20, 2012, 16 pages.
Response to Office Action dated Jul. 20, 2012 for U.S. Appl. No. 12/876,316, filed Jan. 17, 2013, 25 pages.
Office Action for U.S. Appl. No. 12/876,316 dated Feb. 26, 2013, 19 pages.
Boos et al., "A New, Lightweight Fetal Telemetry System", Dec. 1995 Hewlett-Packard Journal, pp. 82-93.
Letter dated Sep. 9, 2013 to Foreign Associate Uhthoff, Gomes, Vega, & Uhthoff, S.C., providing instructions for Amendment of Claims, for Mexican Pat. Appl. MX/a/2007/015295, 5 pages.
Letter dated Jun. 26, 2013 from Foreign Associate Uhthoff, Gomes, Vega, & Uhthoff, S.C., reporting Notice of Allowance for Mexican Pat. Appl. MX/a/2007/015295, 2 pages.

(56) References Cited

OTHER PUBLICATIONS

Notice of Allowance and Fees Due dated Jul. 2, 2013 for U.S. Appl. No. 13/785,713, 15 pages.
Office Action dated Jul. 25, 2013, for U.S. Appl. No. 13/344,018, 35 pages.
Notice of Allowance and Fees Due dated Jun. 27, 2013, for U.S. Appl. No. 13/192,022, 8 pages.
Office Action dated Jul. 23, 2013, for U.S. Appl. No. 12/876,316, 33 pages.
Communication Pursuant to Article 94(3) EPC dated Aug. 13, 2013, for European Appl. No. 07 254 691.4, 5 pages.

* cited by examiner

ECG LEAD SET AND ECG ADAPTER SYSTEM

BACKGROUND

1. Technical Field

The present disclosure relates to medical equipment. In particular, the present disclosure relates to an ECG lead set, adapter system and methods for coupling an ECG lead set with an incompatible ECG device that may monitor or record ECG signals, hereinafter referred collectively as an "ECG monitor."

2. Description of Related Art

Electrocardiograph (ECG) monitors are widely used to obtain biopotential signals containing information indicative of the electrical activity associated with the heart and pulmonary system. To obtain biopotential signals ECG electrodes are applied to the skin of a patient in various locations and coupled to an ECG monitor. Placement of the electrodes is dependant on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone on the upper chest and a third electrode adjacent the patient's lower left abdomen. A 5-lead configuration requires the placement of the three electrodes in the 3-lead configuration with the addition of a fourth electrode adjacent the sternum and a fifth electrode on the patient's lower right abdomen. A 12-lead configuration requires the placement of 10 electrodes on the patient's body. Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III). The ten electrodes provide 12 measurement points consisting of Leads I, II, III, AVL, AVR, AVF, and V1-V6 with the right leg electrode typically used as a ground.

Electrodes, after placement on the patient, connect to an ECG monitor by an ECG lead set. One end of the ECG lead set, closest to the patient, connects to each electrode (alternatively, the electrodes may be integrated into the distal end of the ECG lead set) and receives biopotential signals from the body. The other end of the ECG lead set connects to the ECG input connector and supplies the biopotential signals received from the body to the ECG monitor.

ECG monitors and ECG lead sets are manufactured and sold by various companies. Although protocols have been established for the placement ECG electrodes, the various manufacturers typically use product specific connectors and wiring configurations.

Problems occur when an ECG lead set and an ECG monitor are electrically incompatible but have mechanically compatible connectors. While some problems may be automatically detected by the monitor, other problems, such as, for example, the incorrect order of V1-V6, may go undetected and the ECG monitor may provide the clinician with erroneous information.

Some ECG monitors are configured to connect to a specific type or family of ECG lead sets manufactured, distributed and sold by the same manufacturer of the ECG monitor. The ECG monitor, and specific type or family of ECG lead sets, may utilize, as a safety feature, a unique or specialized connector that is only compatible with the particular ECG monitor and incompatible with all other ECG lead sets.

While this safety feature may prevent a clinician from accidentally connecting an incompatible lead set to an ECG monitor, it also required each medical facility to supply a plurality of ECG lead sets for the various ECG monitor used within a medical facility.

The present application provides an ECG lead set, adapter system and methods for coupling a standard ECG lead set with any incompatible ECG monitor thus preventing the aforementioned problems.

SUMMARY

The present disclosure relates to medical equipment. In particular, the present disclosure relates to an ECG lead set, adapter system and methods for coupling an ECG lead set with an incompatible ECG monitor.

In accordance with one embodiment, a method for coupling an ECG monitor with an incompatible ECG lead set, comprising the steps of providing an ECG adapter including an adapter body with at least one monitor connector and at least one lead set receptacle, coupling the monitor connector of the adapter body with the input of an ECG monitor and coupling the lead set receptacle of the adapter body with the connector of an ECG lead set to thereby electrically couple the ECG lead set with the ECG monitor. The at least one monitor connector may be adapted for coupling to an input of an ECG monitor. The at least one lead set receptacle is adapted for coupling to a connector of an ECG lead set incompatible with the input of the ECG monitor.

The step of coupling the at least one lead set receptacle may include connecting one of a six conductor Registered Jack (RJ25) style (or modular) connector and an eight conductor (RJ45) connector of the ECG lead set.

In a further embodiment of the present disclosure, the adapter body includes first and second lead set receptacles and the step of coupling the at least one lead set receptacle includes coupling the first and second ECG lead sets to the respective first and second lead set receptacles. The step of coupling the at least one lead set receptacle may include connecting an RJ25 connector of the first ECG lead set to the first lead set receptacle and connecting an RJ45 connector of the second ECG lead set to the second lead set receptacle.

In yet another embodiment of the present disclosure the ECG adapter system for coupling an ECG lead set with an incompatible ECG monitor includes at least one ECG adapter having at least one monitor connector and at least one lead set receptacle. The at least one monitor connector is adapted for coupling to an input of an ECG monitor. The at least one lead set receptacle is different from the at least one monitor connector and is adapted for coupling to a connector of an ECG lead set incompatible with the input of the ECG monitor. The at least one monitor connector may be a plug and the at least one connector may be a receptacle. Plug and/or receptacle may be one of an RJ25 connector and an RJ45 connector of the ECG lead set.

The adapter body may include a first and second lead set receptacles for coupling to connections of a respective first and second ECG lead sets. The first lead set receptacle is different from the second lead set receptacle to permit coupling to different ECG lead sets. The first lead set receptacle of the adapter body may be adapted for coupling to an RJ25 connector of the first ECG lead set and the second lead set receptacle of the adapter body may be adapted for coupling to an RJ45 connector of the second ECG lead set.

In a further embodiment, the ECG adapter system may include first and second ECG adapters. The at least one monitor connector of the adapter body of the first ECG adapter may be different than the at least one monitor connector of the adapter body of the second ECG adapter. The first and second ECG adapters may couple to the inputs of different ECG monitors.

At least a portion of the plurality of wires of the at least one lead set may form at least one ribbon cable. At least one of the plurality of wires forming the at least one ribbon cable may be separable from the at least one ribbon cable.

In yet another embodiment of the present disclosure, an ECG lead set system includes an ECG lead set including a plurality of lead wires for coupling to a plurality of electrodes, a plug connector coupled to one end of the ECG lead set and an adapter adapted for coupling the plug connector to an input of an ECG monitor. The adapter may include an adapter body having a lead set receptacle for coupling to the plug connector of the ECG lead set and a monitor plug different from the plug connector for coupling to the input of the ECG monitor.

The ECG lead set system may include an electrode connector coupled to the other end of the ECG lead set. The electrode connector may be selected from a group consisting of a snap connector, a wire dumbbell connector, a locking slot connector and a keyhole connector. The ECG lead set system may further include at least one ECG electrode connected to the electrode connector of the ECG lead set. Alternatively, at least one ECG electrode may be pre-wired to the other end of the ECG lead set.

The ECG lead set system may further include a sheath for housing at least a portion of the ECG lead set.

In a further embodiment of the present disclosure, at least a portion of the plurality of lead wires of the ECG lead set may form a ribbon cable. At least a portion of one of the plurality of lead wires, forming the ribbon cable, is separable from the ribbon cable.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. As used herein and as is traditional, the term "distal" refers to the portion which is furthest from the user/clinician and the term "proximal" refers to the portion that is closest to the user/clinician. In addition, terms such as "above", "below", "forward", "rearward", etc. refer to the orientation of the figures or the direction of components and are simply used for convenience of description.

Figure 1:
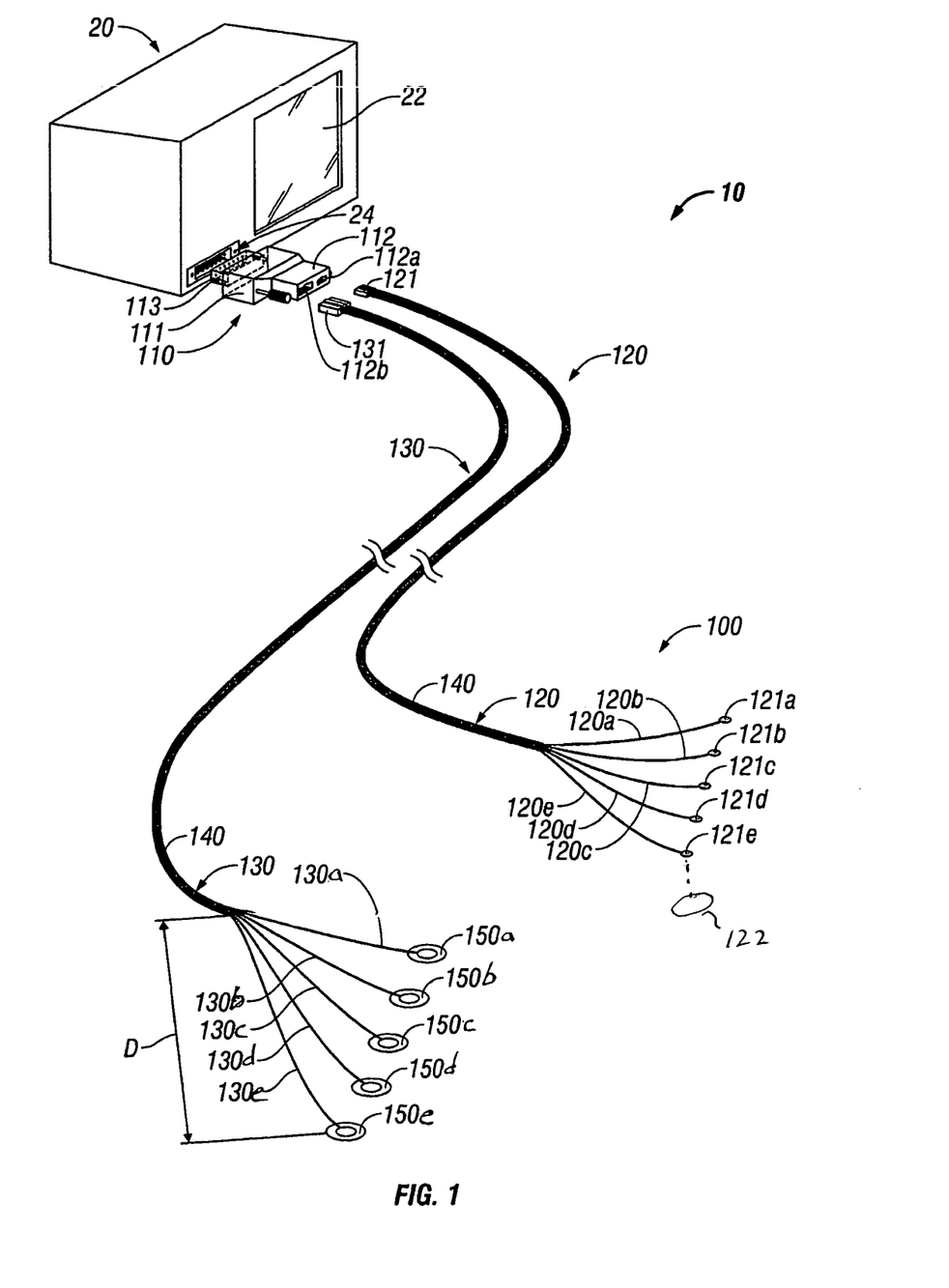
FIG. 1 is a schematic of an ECG monitoring system incorporating an ECG adapter system in accordance with the present disclosure.

FIG. 1 shows an ECG monitoring system 10 incorporating an ECG adapter system 100 according to the present disclosure. The ECG monitoring system 10 includes an ECG monitor 20 and an ECG adapter system 100 that includes an adapter 110 and one or more ECG lead sets 120, 130.

The ECG monitor 20 is configured to receive biopotential signals containing information indicative of the electrical activity associated with the heart and pulmonary system and to display the information on a user display 22. EGC monitor 20 includes at least one lead set input connector 24 configured to connect with at least one compatible ECG lead.

ECG adapter system 100 includes an adapter 110 and one or more ECG lead sets 120, 130. Each ECG lead set 120, 130 includes a plurality of lead wires 120a-e, 130a-e at least partially surrounded by a sheath 140. Sheath 140 may protect lead wires 120a-e, 130a-e from physical damage or may shield lead wires 120a-e, 130a-e from electrical interference. The sheath 140 of the ECG adapter system 100 may vary in length between about 2 to 10 feet.

At least a portion of lead wires 120a-e, 130a-e extends distally from sheath 140 a distance "d", between about 2 to 40 inches. The distal end of lead wires 120a-e may connect to one or more electrode connectors 121a-e. Electrode connectors are configured to connect to an ECG electrode 122 shown separated from electrode connector 121e. Alternatively, lead wires 130a-e may be integrated into the electrodes 150a-e. One or more electrodes 150a-e may be coupled to the distal end of each individual lead wire 130a-e or electrode may be formed from the and individual lead wire 130a-e.

FIGS. 3A-3D illustrate various electrode connectors 221a-d that may be attached to, or formed on, the distal end of a lead wire 220a-b. Distal end of lead wire 220a may attach to an electrode connector, such as, for example, a snap connector 221a, a locking slot connector 221e or a keyhole connector 221d. Alternatively, distal end of lead wire 220b may form the electrode connector, such as, for example, a dumbbell connector 221b. Additionally, the standard snap or pinch clip connectors and others known in the field may terminate the distal end of the leadwire.

Figure 3A:
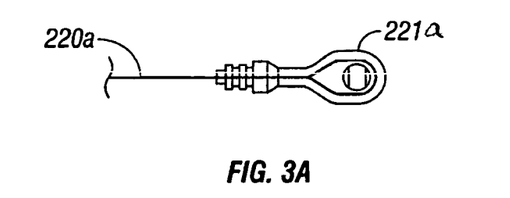
FIGS. 3A-3F are schematics of various electrode connectors and electrodes that may be used to form the ECG adapter system of the present disclosure.
Figure 3B:
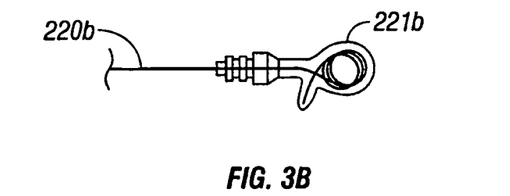
Figure 3C:
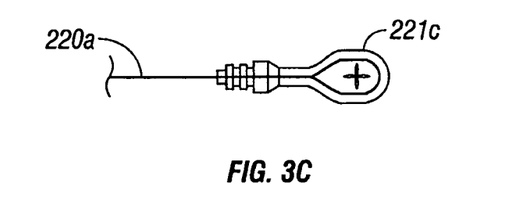
Figure 3D:
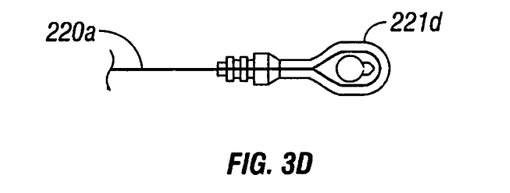
Figure 3E:
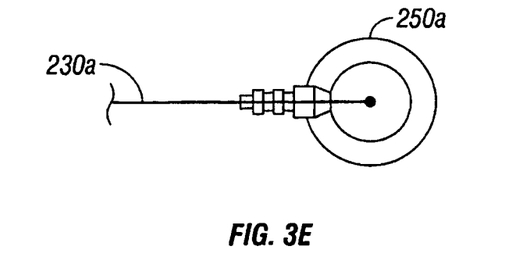
Figure 3F:
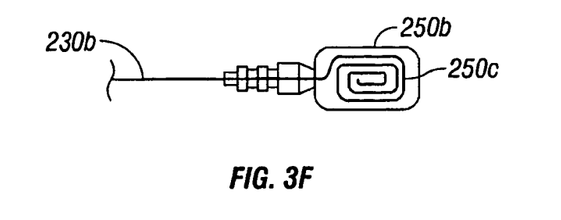

FIG. 3E is a schematic of an electrode 250a attached to the distal end of lead wire 230a. Alternatively, as illustrated in FIG. 3F, the distal end of the lead wire 230b may form the conductive portion 250c of the electrode 250b.

Irrespective of the electrode configuration, (e.g., electrode connectors, pre-wired and/or integrated electrodes) in use the electrodes are connected to the ECG lead set 120, 130, disposed on a the patient and configured to received the biopotential signals.

Lead set connector 121, 131 is coupled to the proximal end of the ECG lead set 120, 130 and configured to couple with adapter 110. Adapter 110 includes at least one lead set receptacle 112a, 112b to electrically couple to the lead set connector 121, 131. Adapter 110 electrically couples the ECG lead sets 120, 130 of the ECG adapter system 100 with the ECG monitor 20.

Sheath 140 may be integrated into the lead set connector 121, 131 or may be formed from a suitable tubular member and coupled to the lead set connector 121, 131.

ECG lead set 120, 130 may be formed from a plurality of individual wires or from a suitable cable containing a plurality of wires, such as, for example, a multi-conductor shielded cable or ribbon cable. Sheath 140 may be the cable jacket or may be a separate tubular member at least partially surrounding a portion and/or length of the plurality of individual wires or cable.

Adapter 110 includes an adapter body 111 with an input receptacle 112 and a monitor plug 113. Input receptacle 112 includes at least one lead set receptacle 112a, 112b configured to couple to a lead set connectors 121, 131 of an ECG lead set 120, 130. Monitor plug 113 is configured for coupling to the lead set input connector 24 of the ECG monitor 20. Lead set connectors 121, 131 of the ECG lead sets 120, 130 are different than monitor plug 113 of the adapter 110 such that lead set connectors 121, 131 are not configured to connect to the lead set input connector 24 of the ECG monitor 20. The difference between the lead set connectors 121, 131 and the monitor plug 113 must be such that the lead set connectors 121, 131 are mechanically incompatible and/or physically incompatible with the lead set input connector 24 of the ECG monitor 20.

Monitor plug 113 of adapter 110 is configured to connect to a specific ECG monitor 20 and may include any safety feature or unique/specialized aspect required to allow monitor plug 113 to connect with the lead set input connector 24 of the ECG monitor 20. A separate, and possibly unique, adapter 110 may be required for each ECG monitor 20. The lead set receptacles 112a, 112b of the various adapters 110, irrespective of the ECG monitor 20 that it connects to, may be configured to accept the lead set connectors 121, 131 of the ECG lead set 120, 130. Lead set receptacles 112a, 112b are electrically coupled to the monitor plug 113 such that the ECG lead set 120, 130, which is otherwise incompatible with the ECG monitor 20, connects to ECG monitor 20. The adapter 110 couples an ECG lead set 120, 130 with an ECG monitor 20, wherein the lead set input connector 24 of the ECG monitor 20 and the lead set connector 121, 131 of the ECG lead set 120, 130 are otherwise incompatible.

Lead set connector 121, 131 and the respective mating lead set receptacle 112a, 112b may be formed of standard connectors. Lead set connectors 121, 131 and lead set receptacles are formed with connectors not presently associated or used with current ECG monitors, such as, for example, but not limited to, RJ45 and RJ25 telephone connectors commonly used in the telecommunications industry but not presently associated with ECG monitors. Alternatively, lead set connectors 121, 131 and lead set receptacles 112a, 112b may be designed and/or constructed specifically for this application.

In use, the lead set connector 121, 131 couples to the respective lead set receptacle 112a, 112b. For example, lead set connector 121 may be an RJ25 connector and may connect to an RJ25 lead set receptacle 112a of the adapter receptacle 112. Similarly, lead set connector 131 may be an RJ45 connector and may connect to an RJ45 lead set receptacle 112b of the adapter receptacle 112. Monitor plug 113 couples to the lead set input connector 24 of the ECG monitor 20 thereby electrically connecting electrode connectors 121a-e and/or electrodes 150a-e to the ECG monitor 20. As a further alternative, RJ11, RJ14 and RJ50 lead set connectors and corresponding receptacles are also envisioned.

Figure 2A:
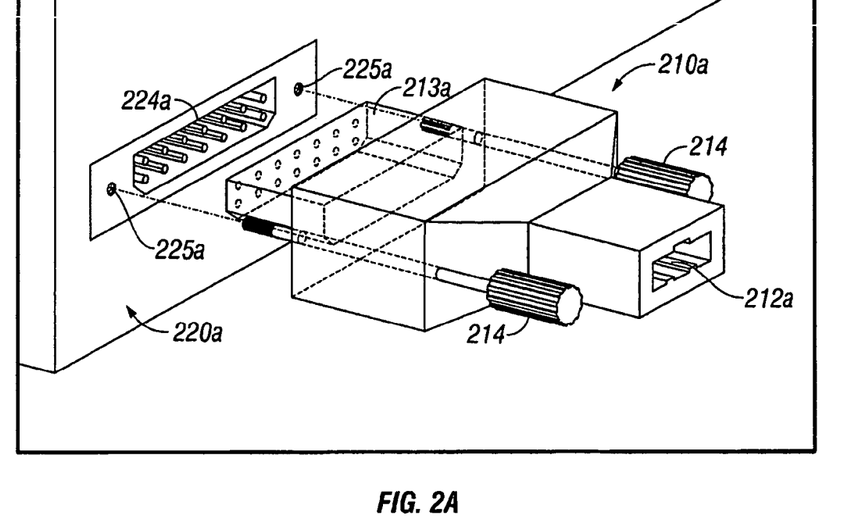
FIGS. 2A-2C are schematics of variations of the adapter from the ECG adapter system of FIG. 1.

Variations of the adapter 110 from FIG. 1 are illustrated in FIGS. 2A-2C. In FIG. 2A, the adapter 210a include a monitoring plug 213a configured to connects to input connector 224a of ECG monitor 220a. The input connector 224a on ECG monitor 220a may be configured to receive a lead set connector that may connect one or more types of lead sets to the ECG monitor 220a, e.g., configured to connect to a 3-lead lead set, a 5-lead lead set and/or a 12-lead lead set. Lead set receptacle 212a on adapter 210a may also be configured to connect to a single type of lead set connector that may connect to a 3-lead lead set, a 5-lead lead set and/or a 12-lead lead set, or other types of ECG lead sets, and configured as an ECG lead sets described herein. Lugs 214 on adapter 210a may connect to terminals 225a on ECG monitor 220a.

Figure 2B:
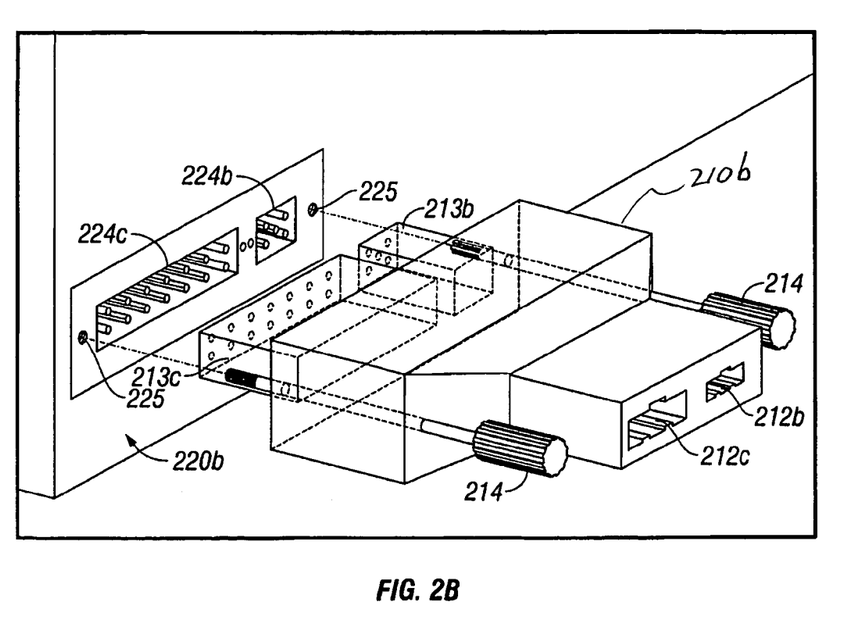

In FIG. 2B, adapter 210b includes two monitoring plugs 213b, 213c that connect to a first input connector 224b and a second input connector 224c of ECG monitor 220b. First input connector 224b of the ECG monitor 220b may be configured to receive a first type of ECG Lead set, such as, for example, a 3-lead EGC lead set, and second connector 224c of the ECG monitor 220b may be configured to receive a different type of ECG lead set, such as, for example, a 5-lead ECG lead set or a 12-lead ECG lead set. Adapter 210b may include a first lead set receptacle 212b and a second lead set receptacle 212c configured to connect to an ECG lead set of the present disclosure as described herein.

Figure 2C:
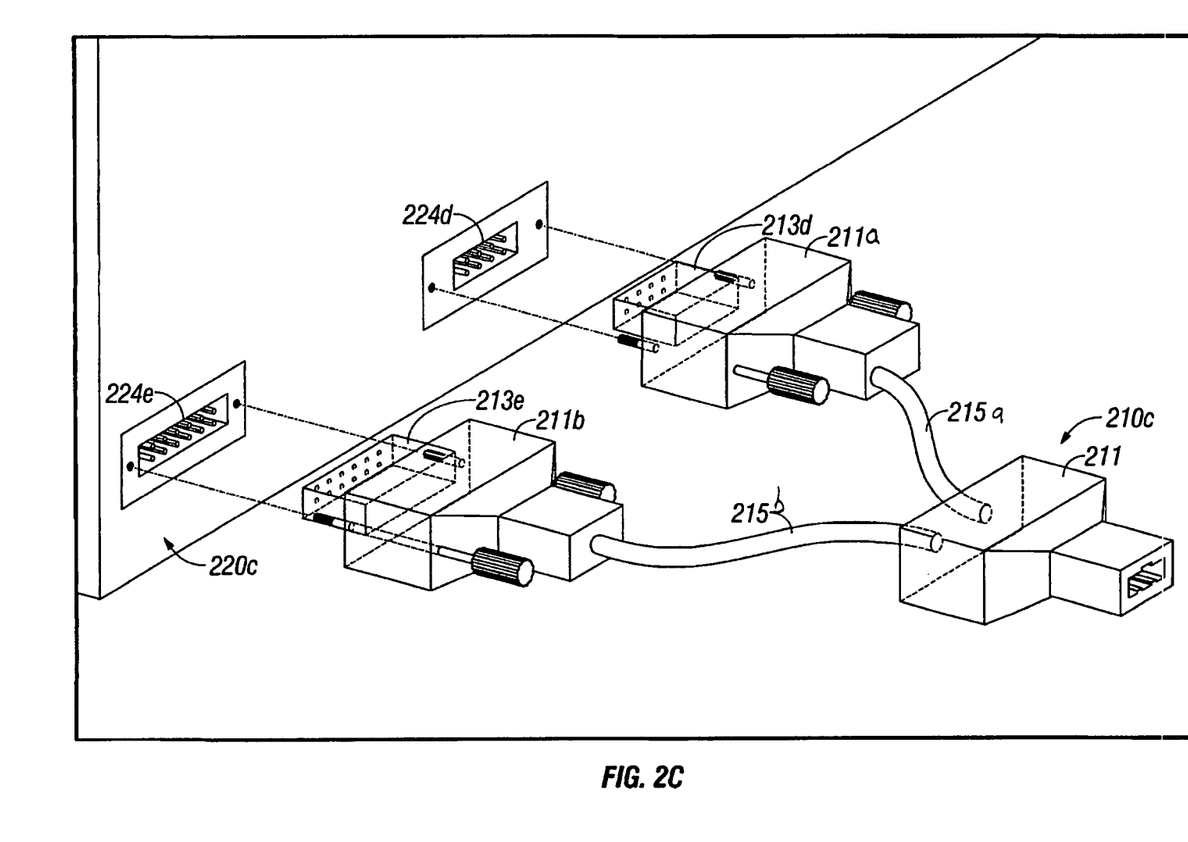

In FIG. 2C, adapter 210c includes an adapter body 211 and one or more remote adapter bodies 211a, 211b having one or more monitor plugs 213d, 213e. Monitor plugs 213d, 213e are configured to connect with first and second input connectors 224d, 224e, respectively, of the ECG monitor 220c. First and second adapter bodies 211a, 211b are connected to the adapter body 211 through cable 215a, 215b or other suitable means of forming an electrical and/or mechanical connection.

Other suitable variations of a monitor plug required to connect an adapter of the present disclosure to various other ECG monitors are contemplated and within the scope of this disclosure.

Figure 4A:
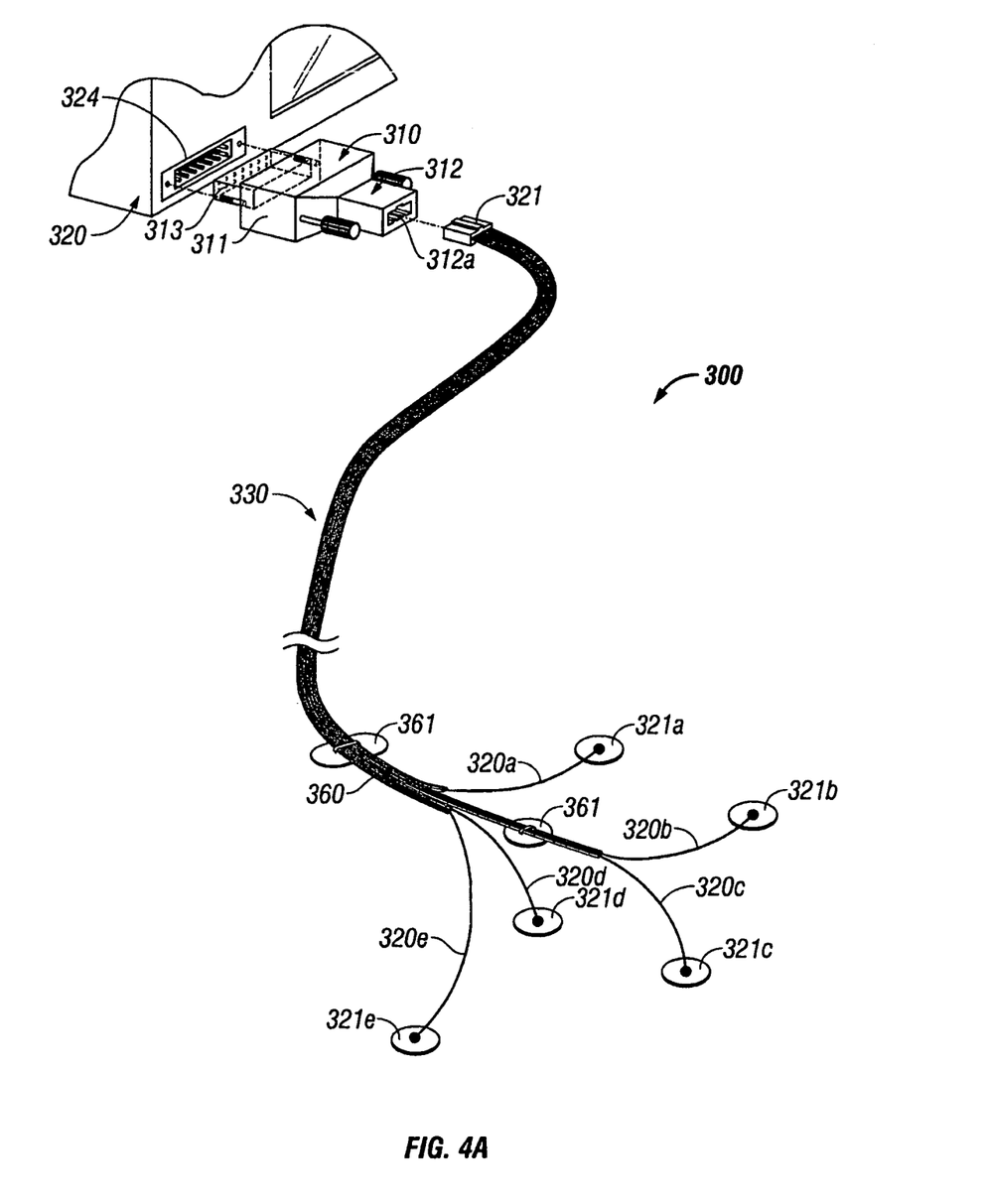
FIG. 4A is a schematic of another embodiment of the ECG adapter system of the present disclosure with the lead wires forming a separable ribbon cable.

FIG. 4A is yet another embodiment of an ECG adapter system 300 including an adapter 310 and an ECG lead set 330 having a separable or tearable ribbon cable 360. A lead set connector 321 is coupled to the proximal end of the ribbon cable 360 and a plurality of electrodes 321a-e, or plurality of electrode connectors (not shown), are coupled the distal end of the individual lead wires 320a-320e. One or more adhesive backed sliders 361 may be slidably disposed on a portion of the ribbon cable 360.

Adapter 310 includes an adapter body 311, an input receptacle 312 and a monitoring plug 313. Input receptacle 312 includes at least one lead set receptacle 312a. Lead set receptacle 312a may be configured to receive an RJ25 connector or any other suitable receptacle or connector may be used. Monitoring plug 313 is configured to connect to an input connector 324 of an ECG monitor 320.

Figure 4B:
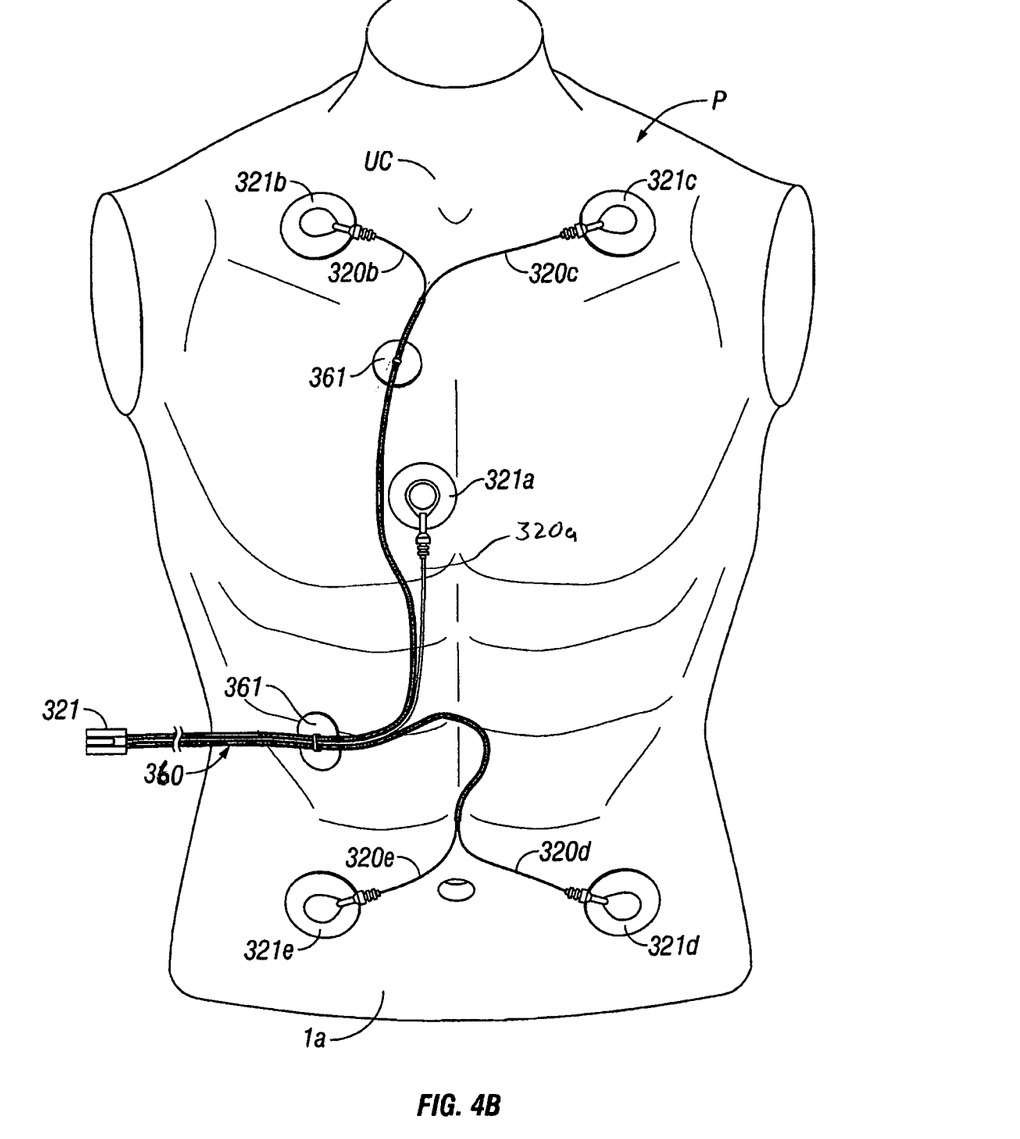
FIG. 4B illustrates the ECG adapter system of FIG. 4A placed on a patient.

In use, as illustrated in FIG. 4B, the distal portion of one or more individual lead wires 320a-320e may separated from, or may be pulled away from, one or more of the remaining lead wires forming the ribbon cable 360 in order to increase the distal portion of an individual lead wires 320a-320e separated from the ribbon cable 360 or from the other individual lead wires 320a-320e. For example, distal end of lead wires 320e and 320d may be further separated from the ribbon cable 360 such that the respective electrodes 321d, 321e may be disposed on the lower abdomen "la" of patient "p". Similarly, distal end of lead wires 320b and 320c are further separated from each other such that the respective electrodes 321b, 321c may be disposed on the patient "p" adjacent the left and right side of the upper chest "uc". Adhesive backed sliders 361 may be positioned on the ribbon cable 360 and disposed on the patient "p" to secure ECG adapter system 300 on the patient "p" and/or to prevent further separation of the ribbon cable 360.

In a further embodiment of the present disclosure, ribbon cable 360 of the ECG adapter system 300 may include a plurality of layers to electrically shield the wires of the ribbon cable 360 from electrical interference or noise. Alternatively, lead wires 320a-320e that form the ribbon cable 360 may be individually shielded.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method to couple an electrocardiograph (ECG) monitor with at least one ECG lead set, the method comprising:
    providing an ECG monitor having at least one input;
    providing the at least one ECG lead set, wherein a number of the at least one ECG lead set is different from a number of the at least one input;
    determining the number of the at least one input and a configuration of each input;
    determining the number of the at least one ECG lead set and a configuration of a lead set connector of each ECG lead set;
    selecting an ECG adapter from a plurality of ECG adapters according to the number of the at least one input, the configuration of each input, and the number of the at least one ECG lead set, the plurality of ECG adapters comprising at least two ECG adapters configured to connect to a different number of ECG lead sets from each other, the selected ECG adapter comprising:
        a monitor connector for each input, each monitor connector corresponding to one of the inputs for coupling the ECG adapter to each input; and
        a lead set receptacle for each ECG lead set, each lead set receptacle corresponding to one of the lead set connectors for coupling the ECG adapter to each ECG lead set;
    coupling the ECG adapter to the ECG monitor such that each monitor connector is coupled to the corresponding input; and
    coupling the ECG adapter to each of the lead set connectors to thereby electrically couple the ECG lead sets with the ECG monitor.

2. The method of claim 1, wherein coupling the ECG adapter to the ECG monitor and coupling the ECG adapter to each of the lead set connectors comprises coupling first and second ECG lead sets to a single input of the ECG monitor.

3. The method of claim 1, wherein coupling the ECG adapter to the ECG monitor and coupling the ECG adapter to each of the lead set connectors includes coupling a single ECG lead set to first and second inputs of the ECG monitor.

4. The method of claim 1, further comprising obtaining biopotential signals with each ECG lead set for reception by the ECG monitor.

5. The method of claim 1 wherein coupling the ECG adapter to each of the lead set connectors comprises coupling the ECG adapter to at least one of a six conductor Registered Jack (RJ) connector or an eight conductor RJ connector.

6. The method of claim 1 wherein coupling the ECG adapter to each of the lead set connectors comprises coupling the ECG adapter to at least one of an RJ25 connector or an RJ45 connector.

7. The method according to claim 1 wherein selecting the ECG adapter comprises selecting an ECG adapter comprising a first lead set receptacle and a second lead set receptacle, and
    wherein coupling the ECG adapter to each of the lead set connectors comprises mechanically engaging each of the ECG lead sets to the respective first and second lead set receptacles.

8. The method of claim 7 wherein mechanically engaging each of the ECG lead sets to the respective first and second lead set receptacles comprises connecting an RJ25 connector of a first ECG lead set to the first lead set receptacle and connecting an RJ45 connector of a second ECG lead set to the second lead set receptacle.

9. The method of claim 1 wherein coupling the ECG adapter to the ECG monitor comprises mechanically engaging at least one monitor connector of the adapter with an input of the ECG monitor.

10. The method of claim 1 wherein coupling the ECG adapter to each of the lead set connectors comprises mechanically engaging at least one lead set receptacle of the adapter with a connector of an ECG lead set.

11. The method of claim 1 wherein selecting an ECG adapter from a plurality of ECG adapters according to the number of the at least one input, the configuration of each input, and the number of the at least one ECG lead set further comprises selecting an ECG adapter from a plurality of ECG adapters according to the number of the at least one input, the configuration of each input, the number of the at least one ECG lead set and the configuration of a lead set connector of each ECG lead set.

* * * * *